United States Patent [19]

Kiesow

[11] 4,014,649
[45] Mar. 29, 1977

[54] METHOD AND APPARATUS FOR DELIVERING BLOOD OXYGEN ASSOCIATION CURVE INFORMATION

[75] Inventor: Lutz A. Kiesow, Bethesda, Md.

[73] Assignee: Baxter Travenol Laboratories, Inc., Deerfield, Ill.

[22] Filed: Apr. 12, 1976

[21] Appl. No.: 675,703

[52] U.S. Cl. .................. 23/230 B; 23/253 R; 356/39
[51] Int. Cl.$^2$ .................. G01N 21/24; G01N 33/16
[58] Field of Search ............... 23/230 B, 253 R; 356/39, 41, 205, 206

[56] References Cited
UNITED STATES PATENTS

| | | | |
|---|---|---|---|
| 3,740,320 | 6/1973 | Arthur | 23/253 R X |
| 3,779,708 | 12/1973 | Runck et al. | 356/41 X |
| 3,854,878 | 12/1974 | Kiesow | 23/230 B |
| 3,868,223 | 2/1975 | Robock et al. | 23/253 R |
| 3,973,915 | 8/1976 | Raffaele et al. | 23/230 B X |

*Primary Examiner*—Robert M. Reese
*Attorney, Agent, or Firm*—Henry W. Collins; Richard G. Kinney; James T. Fitzgibbon

[57] ABSTRACT

Method of measuring the oxygen association state of blood samples, which includes the steps of disposing a blood sample within a blood-receiving receptacle, providing a controlled atmosphere chamber, incubating the sample by placing it in the chamber and controlling said atmosphere therein so as to maintain the humidity, temperature, and carbon dioxide content of the atmosphere at substantially constant levels, and thereafter analyzing the sample by changing the concentration of oxygen in said chamber from time to time while observing the changes of oxygen association of the sample with respect to the concentration of oxygen within the chamber.

An apparatus which includes two sample holders receiving slides adapted to position the samples in the chamber in incubating and analyzing position, respectively.

7 Claims, 9 Drawing Figures

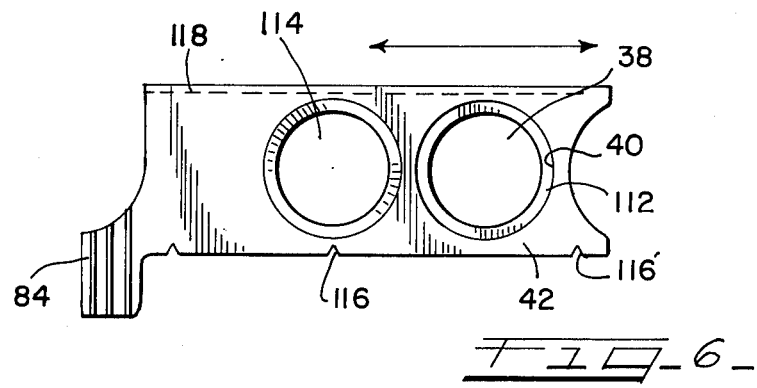
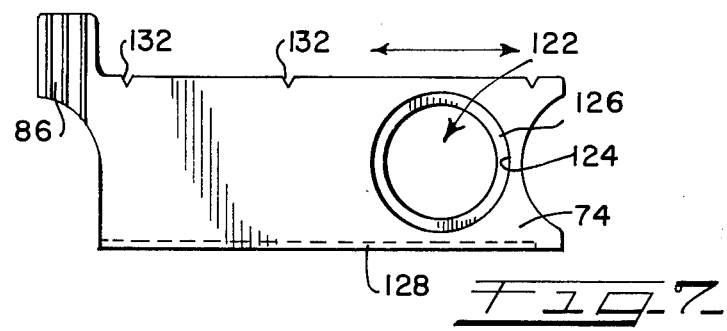
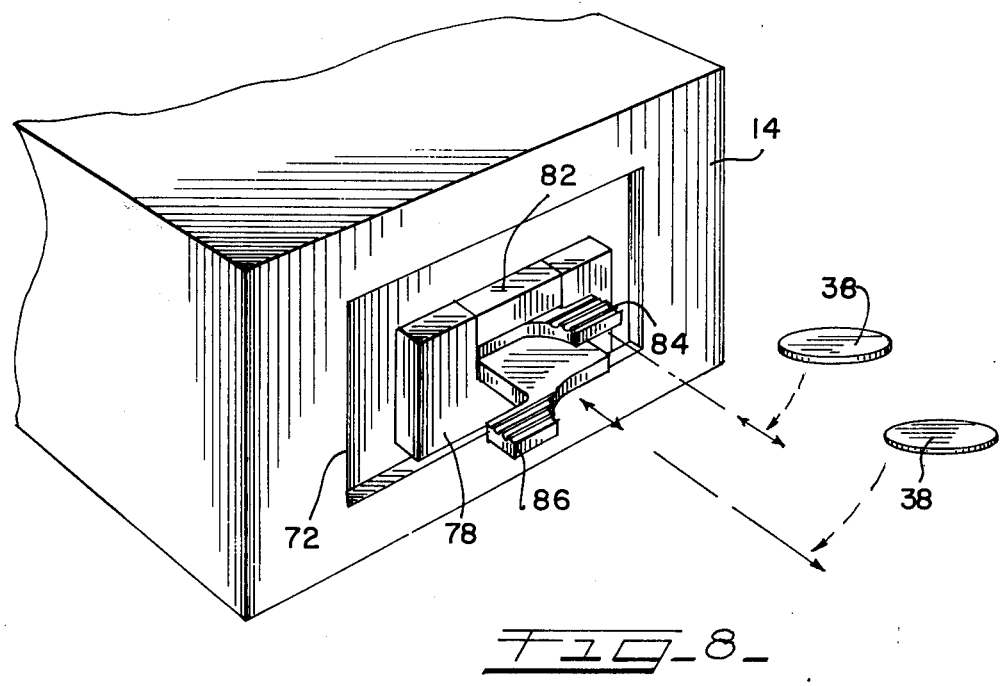

METHOD AND APPARATUS FOR DELIVERING BLOOD OXYGEN ASSOCIATION CURVE INFORMATION

BACKGROUND OF THE INVENTION

The present invention relates generally to improved methods and apparatus for blood analysis, and more particularly to improved methods and apparatus for handling blood samples during a determination of the oxygen association of the blood, and charting the relation between the degree of such association and the concentration of oxygen which is in effective contact with the sample.

Normally, a chart is prepared on an instrument designed to record a series of readings representing the degree of oxygen association existing at any given oxygen concentration. The chart is used for diagnosis of clinical conditions existing in the patient by medical and/or other technicians.

According to the invention, it has been discovered that increased accuracy and reproducibility of these characteristic curves can be obtained if the blood samples are incubated or pre-treated in an atmosphere which is controlled with respect to certain variables before the samples are observed to determine the association curves.

It has also been determined that this pre-treatment or incubation can be achieved without loss of time by using the apparatus and method of the invention; specifically, while one sample is being analyzed in one portion of the analysis device, the other sample may be incubated in another portion of the analysis device. Subsequently, the just-analyzed sample is removed and a new sample is inserted in the analysis device for incubation while the just-incubated sample is being analyzed.

The novel analysis device provides a highly effective seal against atmospheric contamination, and serves to hold two samples, one each in an upper and lower slide unit, respectively. Both slides include recesses adapted to receive the analysis devices, and the upper slide also includes an aperture therein to permit exposure of the sample in the lower slide to the conditioning atmosphere within the chamber while the upper slide is in its axially innermost position. The two slides reciprocate among fully inserted, partially inserted, and withdrawn positions, thereby permitting samples to be analyzed, incubated and withdrawn, respectively.

While the general method of analysis is known, the present invention also comprehends certain improvements in the method other than those referred to above.

While the reasons for the success of the invention are not known with certainty, it is thought possible that the exposure of the blood samples to known degrees of humidity and temperature, and known concentrations of carbon dioxide tends to stabilize the blood mechanically, rendering the samples capable of more accurate analysis.

An object of the present invention is to provide an improved apparatus and method for analyzing blood samples.

Another object of the invention is to provide a blood sample analysis method which includes incubating a blood sample under controlled conditions before analyzing it for oxygen association in relation to oxygen concentration.

Still another object of the invention is to provide an analysis method wherein a series of samples are incubated, analyzed and removed, respectively, with each incubated sample being analyzed as a subsequent sample is being incubated.

Another object is to provide an apparatus which includes plural blood sample holder slides arranged for movement between positions permitting the samples to be inserted or removed, incubated or analyzed, with the slides being operable separately of each other in the sequence referred to herein.

Another object is to provide a method of analysis which includes the use of an optical analysis beam comprised of frequencies not heretofore used for this purpose.

These objects and advantages are achieved by providing a method of blood analysis which includes incubating a blood sample under controlled atmospheric conditions before analyzing it, and by providing a novel sample holder apparatus permitting samples to be so incubated before analysis.

The foregoing and other objects and advantages of the invention, including those inherent therein are achieved in practice by providing a method which includes the steps of placing a blood sample to be analyzed in a chamber wherein the atmosphere may be controlled, and permitting said sample to incubate before analysis of the degree of oxygen association thereof is made. The invention also achieves its objects by providing a novel sample holder analysis device permitting blood samples to be maintained within the controlled atmosphere chamber for incubation and analysis, respectively, with one sample being positioned for analysis while the other is positioned away from the light beam used to make the analysis, in a position for incubation. The invention also achieves improved operating advantages by using wave lengths in the light source which have not been heretofore used for this purpose.

The exact manner in which the foregoing objects and advantages are achieved in practice will become more apparent as reference is made to the following detailed description of the preferred embodiments of the invention set forth by way of example and shown in the accompanying drawings, in which light reference numbers indicate corresponding parts throughout the several figures.

BRIEF DESCRIPTION OF THE DRAWINGS

FIG. 6 is a top plan view of the upper slide unit which receives one of the sample holders containing blood samples;

FIG. 7 is a top plan view of the lower slide unit; and

FIG. 8 is a partial perspective view of the apparatus showing the analysis device disposed in a position of use and forming a part of the front wall of a controlled atmosphere chamber.

DESCRIPTION OF THE PREFERRED EMBODIMENT OF THE INVENTION

While the method and apparatus of the present invention may be practiced in different forms, a description thereof will be made with respect to a process wherein blood samples are prepared, placed within a controlled atmosphere chamber, and analyzed by passage of light therethrough. A strip chart recorder is used to record successive readings which relate the degree of oxygen association of the blood in the sample to the concentration of oxygen present within the chamber. According to the invention, the atmosphere within the chamber is controlled with respect to temperature, humidity and carbon dioxide content, and means are provided for purging the chamber of the carrier gas, or purging the chamber of oxygen, as desired, following which metered amount of oxygen are introduced into the chamber for purposes of reacting with the blood sample. Analysis of blood samples by the method referred to herein is generally known to those skilled in the art. The invention herein comprises an improvement in the inventions described in and claimed in my previously issued U.S. Pat. No. 3,854,878, dated Dec. 7, 1974 and in the method and apparatus described in application Ser. No. 504,112, filed Sept. 9, 1974 in the name of Eugene K. Achter now abandoned, said application in turn being a continuation-in-part of application Ser. No. 466,089, filed May 1, 1974 by Eugene K. Achter now abandoned.

As described in the above identified patents and applications, blood samples are taken to end points consisting of complete oxygen association or substantially no oxygen association, and thereafter they are reoxygenated or deoxygenated in a series of steps, with the degree of association and the relative concentration of oxygen being noted at a plurality of reading points. Subsequently, or simultaneously, a curve is constructed which illustrates the relation of the association of oxygen in the blood to the degree of concentration of oxygen present within the chamber wherein the analysis was made. Charts of this sort having a characteristic tape are useful for clinical purposes.

Figure 1:
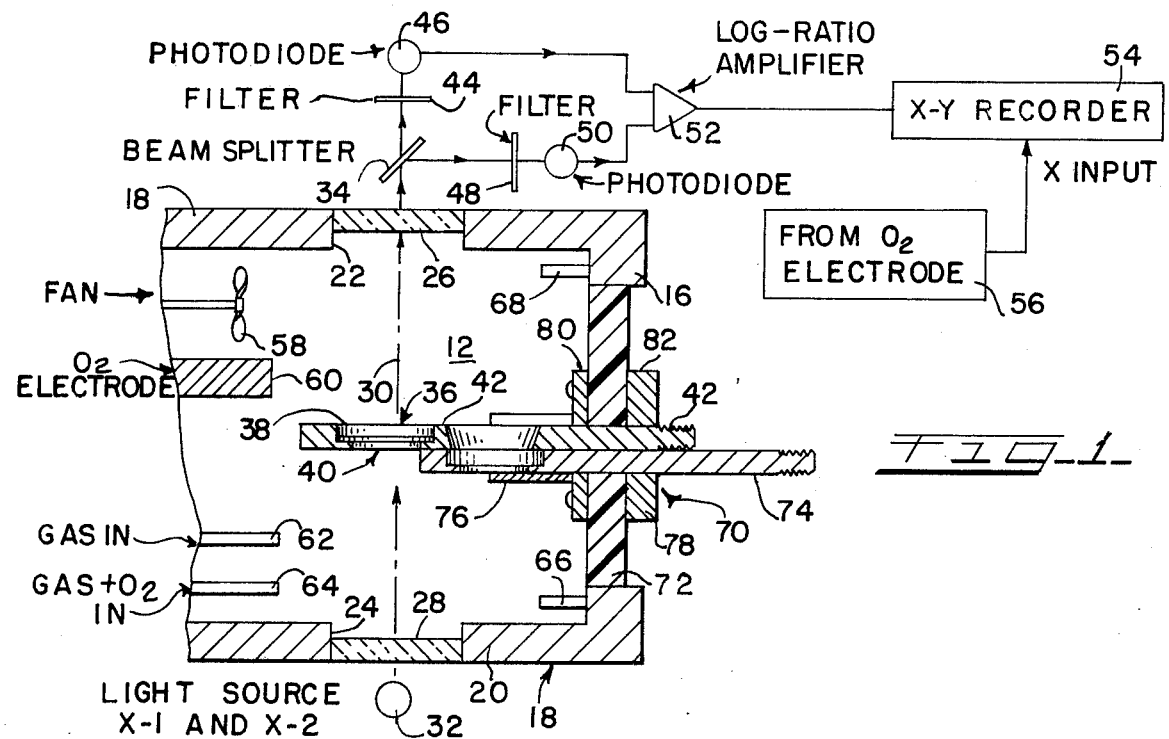
FIG. 1 is a view, partly diagrammatic in character and partly in vertical section, showing one form of apparatus used in the practice of the invention.

Referring now to the drawings, FIG. 1 shows the invention to be typically embodied in an instrument which includes an analysis chamber 12 contained within a housing generally designated 14. The housing 14 is shown to include an end wall 16, a top wall 18 and a bottom wall 20, said walls, together with side walls, (not shown) cooperating to define the enclosed chamber 12. Portions of the top and bottom walls 18, 20 respectively, define top and bottom apertures 22, 24, are placed lenses 26, 28, or other photo transmissive means.

According to the preferred embodiment of the invention, a light beam 30 passes through the lenses 28, 26 from a light source 32 to a beam splitter 34 located outside the chamber. In so doing, the beam 30 passes through the sample 36 which is received in a holder 38 within the pocket 40 of the upper slide unit 42.

As the beam contacts the splitter 34, a portion of it passes therethrough, subsequently through the filter 44, and onto light responsive means in the form of a first photo diode 46. Another portion of the beam is directed from the beam splitter through a second filter 48 and impinges on a second photo diode 50. The outputs of the photo diodes are united in a log-ratio amplifier 52, the output signal of which is directed to an XY-recorder, the operation of which, being known to those skilled in the art, need not be further described. According to this invention, the other input to the XY-recorder 54 is from the oxygen electrode 56. In a preferred form of the invention, a chart is prepared wherein the concentration of oxygen within the chamber forms one axis of chart and the degree of oxygen association forms the other axis, normally the Y-axis. Thus, the curve which results is one wherein the X or horizontal axis shows the concentration of oxygen present and the Y or vertical axis shows a degree of oxygen association within the blood sample. The preferred form of instrument moves the chart within the recorder in response to a signal from the oxygen detector 56.

Referring now again to the make-up of the controlled atmosphere chamber, it will be noted that a fan 58 is provided to insure distribution of the oxygen or other gases in the chamber so that sampling thereof as detected by the oxygen electrode 60 will be accurate. An inlet 62 is provided for a "neutral" or carrier gas 62 as in an inlet for the oxygen-containing gas 64.

As is known to those skilled in the art, the carrier gas is preferably one comprised of nitrogen, having 5.6% $CO_2$ mixed therewith. The oxygen gas consists of 25% oxygen, the same 5.6% $CO_2$ and the remainder nitrogen.

As shown in the drawings, a thermostat schematically shown as 66 is provided, as is a humidity detector 68. In this manner, the atmospheric variables within the chamber 12 may be accurately controlled.

Referring again to FIG. 1, the analysis device generally designated 70 is shown to be contained within a mounting portion 72 which is received within the end wall 16 of the chamber 12. The device 70 includes an upper slide unit 42 and lower unit 74, an inner slide frame 76, an outer slide frame 78, and inner and outer seals 80, 82.

Figures 2, 3, 3A:
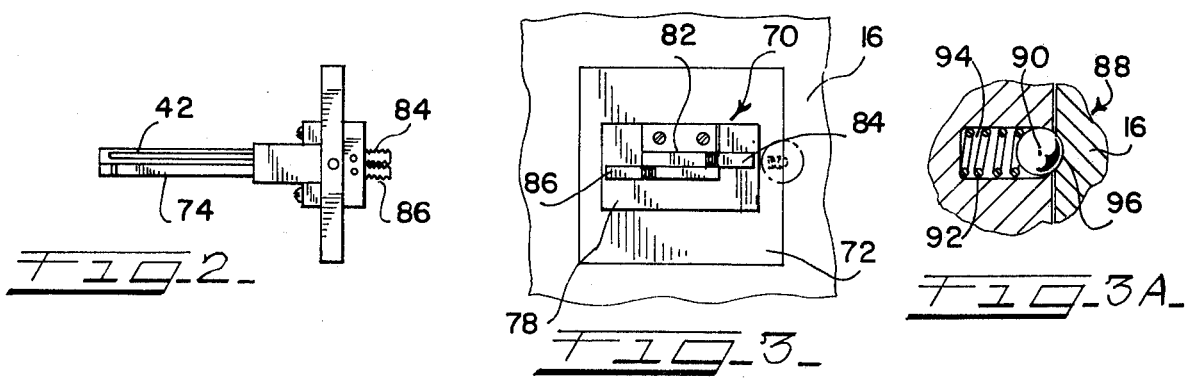
FIG. 2 is a side elevational view of the analysis device, shown apart from the chamber and showing both slide units in the fully inserted position.
FIG. 3 is an end elevational view of the analysis device, showing the manner in which the sample holders are received within the analysis chamber.
FIG. 3a is a fragmentary view, on an enlarged scale, showing the means for retaining the mounting portion of the analysis device assembly within a wall of the chamber.

FIG. 2 shows that the finger receiving portions 84, 86 of the upper and lower slides respectively are flush with each other when both slides are in the forward most position. As shown in FIGS. 3 and 3a, the mounting portion 72 of the analysis device assembly 70 is received within the front wall 16, and is preferably held in place therein by a detent mechanism generally shown at 88. FIG. 3a shows the mechanism 88 to include a ball 90, a spring 92 urging the ball axially of the recess 94 and into a shallow pocket 96 in the end wall 16 of chamber 12. In practice, the opening in the end wall 16 which receives the mounting 72 closely approximates the size of the mounting portion 72 so that a substantially gas type fit between these parts is achieved.

Figures 4, 5:
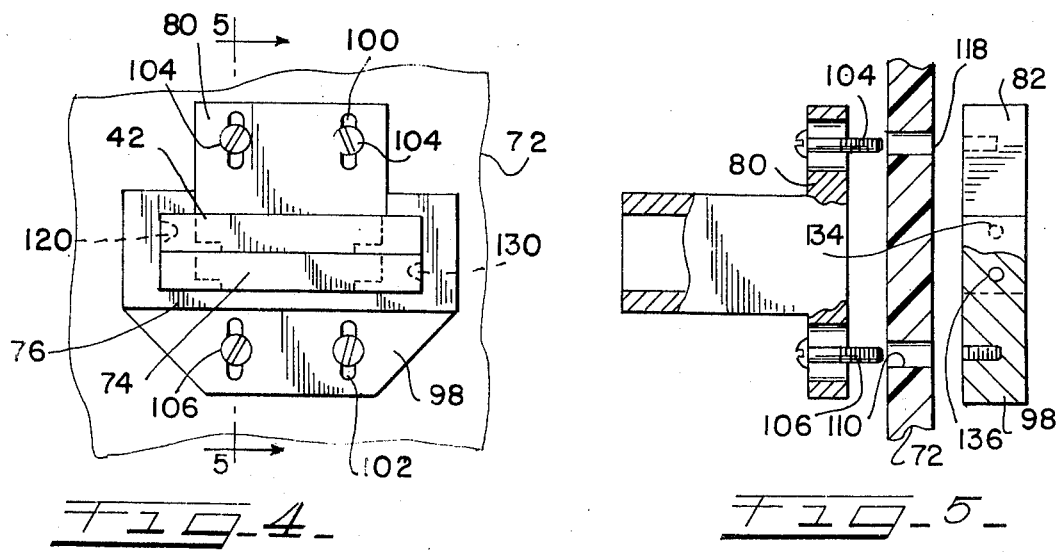
FIG. 4 is an end elevational view, on a enlarged scale, showing the analysis device when viewed from the inside of the chamber.
FIG. 5 is an exploded view, taken approximately along the line 5—5 of FIG. 4, of certain portions of the device, showing the manner of affixing it to the mounting portion of the assembly.

Referring now to FIG. 4, the inner slide frame 76 is shown to be of a generally C-shaped configuration, and to include a mounting bracket 98 extending downwardly therefrom. The upper and lower slides 42, 74 are received within the slide frame, which permits of axial movement of the slides with respect to each other. The top inner seal 80 and the flange 98 are shown to include elongated slots 100, 102 for fasteners 104, 106, thus permitting relative movement of the frames and seals with respect to the mounting portion 72.

FIG. 5 shows that openings 118, 110 in the mounting portion 72 permit the fasteners 104, 106 to extend through the wall 72 and respectively threadly engaged into the outer seal 82 and the outer slide frame 78. With the slides in place within the slide frames, the seals 80, 82 are moved vertically until a snug fit is achieved between them and the upper surfaces of the upper slide 42. Thereupon the fasteners are tightened and effective seal is achieved.

FIG. 6 shows that the upper slide 42 includes a pocket 40 to which the sample holder 38 is received. An inwardly extending annular land 112 prevents the sample holder 38 from falling out of the pocket 40. A venting aperture 114 is also provided in upper slide 42 being axially spaced from the aperture 40 toward the outer or non-entry end of the slide. A thumb receiving, serrated actuator 84 forms the outer or non-entry end of the slide 42. Detent notches 116, 116' are provided along one edge of the slide 42, to insure that the slide will index to a desired axial position which can be detected by the operator. An axially extending groove 118 is provided in the other edge of the slide 42 for receiving a guide boss 120 (FIG. 4).

Referring now to FIG. 7 the lower slide 74 is shown to resemble the upper slide 42 in most respects, but differs therefrom in that there is not venting aperture in slide 74 details. The pocket 122 is defined by a cylindrical wall 124 of the slide and by an inner annularly land extending 126. A glass sample holder 38, to be described later, is received within the pocket 122 in the lower slide 74. Also provided along one edge of the slide 74 is a groove 128 for receiving the boss 130 (FIG. 4) and as well the opposite edge of the slide 74 is provided with detent notches 132 spaced axially therealong. The finger manipulative tab 86 is similar, but located in an opposite hand relation to the position tab 84 of the upper slide 42.

Referring now to FIG. 8, a perspective view of the face of the blood analysis chamber 12 is shown with one slide 74 being disposed partially within the chamber 12 and the other slide 42 being completely inserted therein. The arrows indicate the direction of movement of the respective slides into and out of the chamber, which is only partially shown. As pointed out above, each slide 42, 74 may be indexed in various axial positions within or without the chamber 12, insuring that the sample will be correctly indexed for incubation or viewing, as desired.

Referring again to FIG. 5, it will be noted that the exterior or outer slide frame 78 includes upper and lower detents 134, 136, which engage the notches 116, 132 in slides 42 and 74 respectively. These detents 134, 136 are substantially identical to the structure shown in FIG. 3a being spheres urged by small springs similar to the spring 92 and sphere 96 shown in FIG. 3a.

The sample holders 38 are discoidal in form being adapted to fit within the respective pockets 40 and 122 of the respective slides 42 and 74. Obviously the sample holders may be of a variety of constructions just so long as they are transparent for the passage of light waves and are, at least in part, oxygen permeable so as to permit oxygen to contact the blood sample contained therein. Finally, the diameter or size of the discoidal holder should be such that it will fit within the pockets 40 and 122 and bear against lands 112 and 126 respectively. Preferably the sample holders are of such diameter or size that there is some frictional contact between their outer edges and the cylindrical walls of the aforesaid pockets whereby they will be retained in place yet can be readily expelled from pockets 40 and 122 by modest finger pressure. A most preferred sample holder is the type having a lower glass disc and an upper oxygen permeable membrane of the type described in co-pending application Ser. No. 504,112, filed, Sept. 9, 1974 and including a lower glass and an upper oxygen permeable membrane.

Referring now to the operation of the instrument 10, it will be assumed that a plurality of samples have been prepared by placing blood between a lower glass and an upper oxygen permeable membrane and that the samples have been placed in sample holders. The instrument 10 is operated by turning on the temperature and humidity controls of the known type, typically adjusting conditions inside the chamber 12 to 37° C and 100% relative humidity. A sample holder 38 is placed in the pocket 40 of the upper slide 42, and placed in the chamber. The instrument is calibrated by purging the chamber, first with oxygen so as to completely oxygenate the blood, then with the nitrogen-$CO_2$ mixture so as to completely deoxygenate the blood. Accordingly, the machine will be calibrated for 0% and 100% oxygen. It will be assumed that the first specimen has been incubated within the chamber for a suitable period of time, such as for example, 20 minutes. At this point, a second sample holder is inserted in the apparatus, this time into the pocket 122 in the lower slide 74. The slides are then manipulated to the position shown in FIG. 8 and FIG. 1, with the upper slide 42 fully within the chamber and the lower slide 74 in a intermediate position. This aligns the pocket 40 with the light beam 30. In the position of the slides just described, the venting aperture 114 overlies the pocket 122 in the lower slide 74 permitting contact between the controlled atmosphere and second specimen. Assuming the chamber 12 to have been purged with nitrogen and the sample to be deoxygenated, and further assuming the conditions of temperature, humidity and carbon dioxide to be stabilized, a controlled amount of oxygen containing gas is leaked into the chamber 12 through the inlet 64, which is actually a controlled flow rate, porous plug. The chart recorder is moved in such a way that each increment of additional oxygen occupies a proportional space on the chart recorder, as detected by the oxygen electrode 60. The degree of light absorption within the specimen in sample holder 36 is dependent upon the degree of oxygen association thereof. With plural, continuous readings being taken, comparator receives the signals from the photo diode 46, 50 associated with the respective frequencies, emitting a signal which is received by the recorder 54 and causing the recording pin to deflect. As time elapses, such as a twenty minute period, a trace is made of the oxygen association versus oxygen concentration.

According to the invention, during the time the first specimen is being analyzed by the light beam and the readings are taken, the second specimen disposed within the pocket 122 is being exposed to the controlled conditions of humidity, temperature and carbon dioxide referred to earlier. This pre-conditions the specimens for more accurate reading, and although the reasons therefore are not known with certainty, it is known that a great improvement in accuracy and reproducibility of readings is made possible.

Assuming now that the first specimen has been analyzed, the upper slide 42 is pulled to the outermost position and this sample holder removed. The lower slide 74 is pushed into the innermost position, the upper slide 42 is reloaded with another charged sample holder, and the upper slide indexed to the intermediate position. Thereupon, the chamber 12 is purged, first with oxygen and then with nitrogen, with the instrument being calibrated following each purge. Thereupon the oxygen feed is again initiated, following complete deoxygenation of the sample, and the chart recorder is activated, with the movement thereof along the axis being determined by the output of the oxygen electrode 60. As this process takes place, another strip chart record is made, and the third sample is being incubated. This process may be done as many times as is necessary.

According to the invention, incubated specimens provide the readings of improved accuracy referred to above, without in any way requiring additional time from the chart recorder.

An important feature of the invention is that the samples are not adversely affected by the changing in concentrations of oxygen as the chamber 12 is purged with oxygen and nitrogen respectively at the beginning and end of each recording. In other words, the advantages of incubation are obtained as long as the temperature, humidity, and carbon dioxide concentration are maintained approximately the same. Changing the oxygen concentration as is necessary to obtain the readings on the sample being examined does not affect the sample being incubated. When sample which has been incubated is to be analyzed, the chamber is purged as set forth above. Accordingly, the invention does not require the use of additional time and does not require that special conditions be provided within a chamber to take advantage of incubation. The novel analysis device and slide mechanism provides for a unigue and efficient method and very convenient means for handling the specimens. A relatively tight seal is achieved between the moveable parts of this apparatus and the exterior of the chamber, as set forth above. The slides are manipulated easily and accurately by reason of the alignment grooves and the indexing detents with which the device is provided.

Referring now to another feature of the invention, it has been discovered that the use of two characteristic wave lengths in the light source brings about additional accuracy in analysis. According to the present invention, wave lengths of 576 and 560 nanometers (NM) are preferred. These wave lengths (5760A and 5600A) particularly when used with one or more blue filters, as known to those skilled in the art, produce a more accurate set of readings than has been heretofore found possible with counterpart equivalent. It will thus be seen that the present invention provides a new and useful method and apparatus for analyzing blood samples, such method and apparatus having a number of advantages and characteristics including those referred to specifically herein and others which are inherent in the invention.

A preferred embodiment of the invention having been disclosed by way of example, it is anticipated that certain changes to the apparatus and methods disclosed herein will occur to those skilled in the art, and it is further anticipated that such changes and modifications may be made without departing from the spirit of the invention or the scope of the appended claims, wherein,

What is claimed is:

1. Method of measuring the oxygen association state of blood samples, which includes the steps of disposing a blood sample within a blood-receiving receptable, providing a controlled atmosphere chamber, incubating said sample by placing it in the chamber and controlling said atmosphere therein so as to maintain the humidity, temperature, and carbon dioxide content of the atmosphere at substantially constant levels, and thereafter analyzing the sample by changing the concentration of oxygen in said chamber from time to time while observing the changes of oxygen association of the sample with respect to the concentration of oxygen within the chamber.

2. The method as defined in claim 1 in which two samples are placed within said chamber, with one of said samples being incubated as the other of said samples is being analyzed, with the incubation period comprising at least a portion of the time period during which said other sample is being analyzed.

3. The method as defined in claim 1 in which a series of samples is first incubated and then analyzed, with each of said samples in said series being incubated immediately before being analyzed.

4. A method as defined in claim 1 in which said analysis comprises measuring light absorption within said sample by analysis of a light beam directed through at least a portion of said sample.

5. A method as defined in claim 4 in which said light beam includes elements having respective wave lengths of approximately 576 nm and 560 nm (5760A and 5600A) respectively.

6. An apparatus for incubating and analyzing blood samples, said apparatus comprising, in combination, means defining a sample treating chamber, means for controlling the atmosphere within said chamber, means for receiving at least two blood samples, said receiving means including first and second receiver units mounted for movement between a loading and unloading position, an incubating position, and an analysis position, means for directing a light beam through said chamber, means for detecting the degree of light absorption of a part of said light beam by a sample placed in the path of said beam, and means for preventing substantial leakage of the outside atmosphere into said atmosphere within said chamber.

7. An apparatus as defined in claim 6 in which said receiving units are in the form of slides having sample holder receiving pockets therein, one of said slides overlying the other, with both being arranged for axial movement of said respective pocket portions thereof into and out of said chamber.

* * * * *